United States Patent [19]
Hoy

[11] Patent Number: 5,354,337
[45] Date of Patent: Oct. 11, 1994

[54] BREAST PROSTHESIS SUPPORT

[76] Inventor: Asa T. Hoy, 1134 Gardner, Las Cruces, N. Mex. 88001

[21] Appl. No.: 208,473
[22] Filed: Mar. 10, 1994
[51] Int. Cl.$^5$ ................................................. A61F 2/52
[52] U.S. Cl. .......................................... 623/7; 206/438
[58] Field of Search ..................... 623/7; 206/438, 570

[56] References Cited

U.S. PATENT DOCUMENTS 5,037,436 8/1991 Heaston ................................. 623/7

*Primary Examiner*—Randy C. Shay
*Attorney, Agent, or Firm*—DeWitt M. Morgan

[57] ABSTRACT

A support for a breast prosthesis including a bra cup (of conventional design) which is attached to the perimeter of a cup support member. The cup support member also includes apparatus for positioning the cup from a horizontal surface a distance sufficient to prevent the cup, when holding a prosthesis, from touching such horizontal surface. The positioning apparatus is detachable.

5 Claims, 1 Drawing Sheet

BREAST PROSTHESIS SUPPORT

FIELD OF THE INVENTION

The present invention relates to breast prosthesis supports and, more particularly, to a portable support which can be stored flat when not in use and which, when in use, supports the prosthesis without deformation.

DESCRIPTION OF THE PRIOR ART

A typical breast prosthesis worn after a mastectomy is made of a material simulating the glandular structure in a human female breast. The prosthesis may be characterized as having gelatinous physical behavioral characteristics. As it is flowable within limits it can change form, depending upon its orientation. If the prosthesis is allowed to remain deformed for an extended period of time it will no longer resemble the female breast and becomes unsuitable for its intended use.

When the prosthesis is held in place on its user in a convention manner by a bra or other undergarment, it assumes a configuration simulating the female breast. It is difficult, however, when not in use to store or support the breast in this orientation and accordingly such prostheses are typically stored nipple down in a rigid container having a cavity molded therein to uniformly support the prosthesis and hold it in a desired configuration to eliminate any possibility of deformation.

The problem with supporting breast prosthesis in rigid containers of this conventional type, is that the container itself is, of necessity, slightly larger than the prosthesis. Thus, if the user is travelling she must carry a relatively large package in which the prosthesis can be stored when not in use.

U.S. Pat. No. 5,037,436 to S. K. Heaston discloses a solution to the above identified problem: a bladder which can be selectively inflated and deflated. In its deflated configuration the support can be stored in a relatively flat configuration. It is asserted that the bladder in its inflated condition serves to circumferentially and substantially uniformly engage and support the prosthesis without substantially deforming it.

It is an object of the invention to provide a support for a breast prosthesis which: is light in weight; can be quickly assembled for use; supports the prosthesis without deformation thereof; and disassembles for compact storage.

SUMMARY OF THE INVENTION

A support for a breast prosthesis which has a surface engagable with the chest of a female. The support includes a relatively flat support member having first and second opposing sides and an opening therein. Though slightly larger, the perimeter of the opening has substantially the same configuration as the configuration of the perimeter of the surface of the prosthesis engagable with the chest. The prosthesis support also includes: a bra cup (left or right side, as the case may be) for receiving the prosthesis and means for attaching the perimeter of the cup to the support member. The prosthesis support also includes apparatus for positioning the flat support member relative to a horizontal surface a distance sufficient to prevent the cup, when holding the prosthesis, from touching such horizontal surface. For compact storage this positioning apparatus is detachably attached to the support member.

DESCRIPTION OF THE PREFERRED EMBODIMENT

Figure 1:
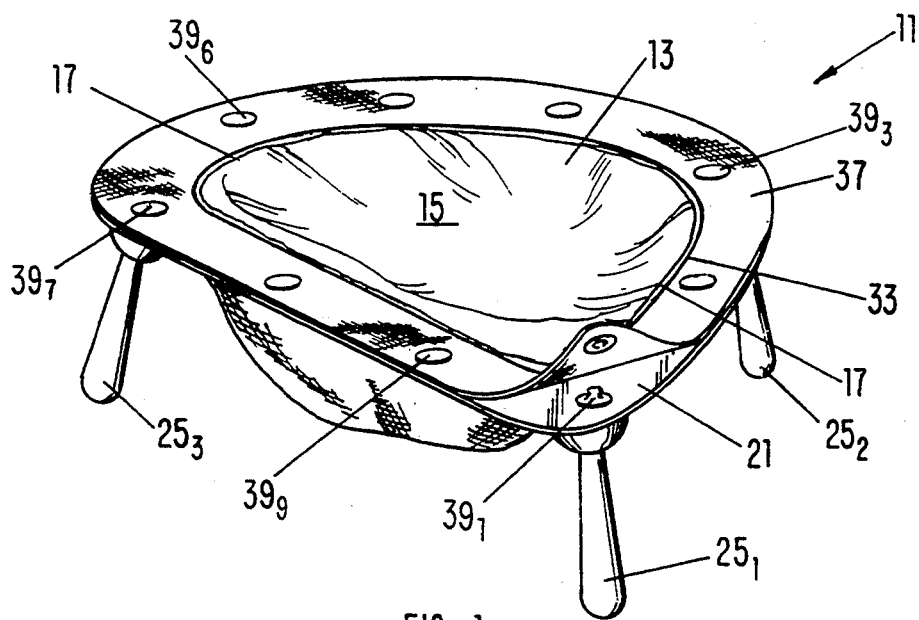
FIG. 1 is a top perspective view of the prosthesis support in its assembled form and supporting a prosthesis.

With reference to FIG. 1, prosthesis support 11 and prosthesis 13 are illustrated. Prosthesis 13, which is formed of gelatinous or other suitable material, has a surface 15 designed for engagement with the chest of a female, and a surface (not shown) simulating the surface of a female breast. As illustrated, surface 15 has in irregular shaped perimeter 17.

Figure 2:
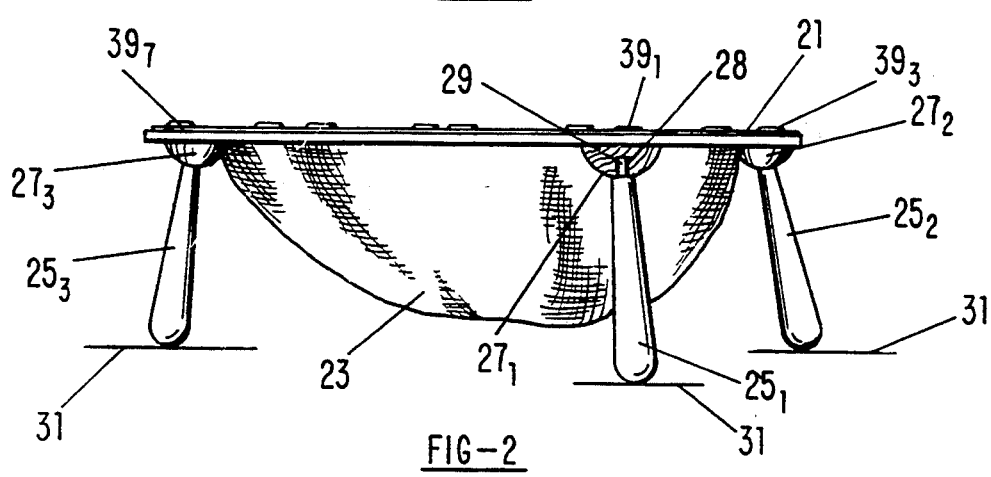
FIG. 2 is a side view of the prosthesis support of FIG. 1.

Prosthesis support 11 includes a support member 21, a fabric cup 23, and three support legs $25_{1-3}$. Support member 21 includes three receptacles $27_{1-3}$. Each receptacle has a cylindrical opening therein, such as exemplified by 28 for slidably receiving the dowel shaped ends of legs 25, such as end 29 of leg $25_1$. See FIG. 2. As is also illustrated in FIG. 2, legs $25_{1-3}$ position support member 21 above horizontal surface 31 (e.g. a table or dresser top) a distance sufficient to prevent cup 23 from touching surface 31 when prosthesis 13 is received therein. As is also illustrated in FIG. 2, the cylindrical openings of receptacles 27 are angled away from cup 23 at an angle of about 10° from horizontal to provide a more stable support.

Cup 23 is preferably made of fabric and is shaped to conform to the surface of prosthesis 13 which simulates the surface of a female breast. Preferably, cup 23 is substantially identical to the cup of a bra which would support the prosthesis when being worn. As illustrated in FIG. 1, the perimeter 33 of cup 23 is irregular shaped, and approximately the shape of prosthesis perimeter 17. The perimeter of support member 21 (not shown) is also irregularly shaped and substantially the same as the shape of perimeter 33. As illustrated, the flange portion 37 of cup 23 is attached to support member 21 via a plurality of snaps $39_{1-9}$. Alternately, velcro or other fasteners could be used. Also, flange 37 could be stitched or glued to support member 21.

Figure 3:
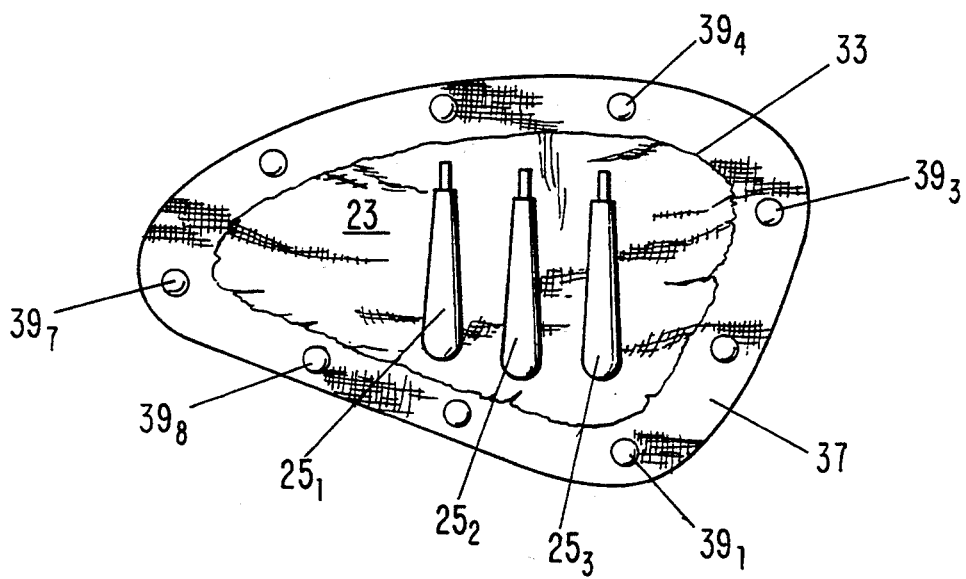
FIG. 3 is a top view of the prosthesis support of the present invention shown in is compact storage position.

In operation dowel ends, such as 29 of legs 25, are received in their receptacles $27_{1-3}$ and prosthesis 13 is placed in cup 23 as illustrated in FIGS. 1 and 2. When not in use, legs $25_{1-3}$ are quickly and easily removed and may be conveniently stored as illustrated in FIG. 3, which is relatively flat for compact storage and travel.

Whereas the drawings and accompanying description have shown and described the preferred embodiment of the present invention, it should be apparent to those skilled in the art that various changes may be made in the form of the invention without affecting the scope thereof.

I claim:

1. A support for a breast prosthesis, said prosthesis having a surface simulating a female breast and a surface engagable with the chest of a female, said engagable surface having a perimeter, said support comprising:
   a. a substantially flat support member having first and second opposing sides and an opening therein, said opening having an irregularly shaped perimeter, said perimeter being slightly larger than and approximating said perimeter of said engagable surface of said prosthesis;

b. a fabric cup configured to support said surface of said prosthesis simulating said breast, said fabric cup having a flange portion;

c. means for securing said flange portion of said fabric cup to one of said first and second sides;

d. means for positioning said flat support member a distance relative to a horizontal surface whereby said fabric cup, when holding said prosthesis, does not touch said horizontal surface; and e. means for detachably attaching said positioning means to said support member.

2. The prosthesis support as set forth in claim 1, wherein said positioning means includes three detachable legs.

3. The prosthesis support as set forth in claim 1, wherein said fabric cup is one cup of a bra.

4. The prosthesis support as set forth in claim 1, wherein said fabric cup is detachably attached to said support member.

5. The prosthesis support as set forth in claim 1, wherein said fabric cup is permanently attached to said support member.

* * * * *